(12) United States Patent
Bills

(10) Patent No.: US 7,234,939 B2
(45) Date of Patent: Jun. 26, 2007

(54) DENTAL INSTRUMENTS HAVING A HANDLE FORMED BY TWO-SHOT MOLDING

(75) Inventor: Dan J. Bills, Salt Lake City, UT (US)

(73) Assignee: Ultradent Products, Inc., South Jordan, UT (US)

(*) Notice: Subject to any disclaimer, the term of this patent is extended or adjusted under 35 U.S.C. 154(b) by 0 days.

(21) Appl. No.: 11/205,593

(22) Filed: Aug. 17, 2005

(65) Prior Publication Data

US 2006/0110704 A1  May 25, 2006

Related U.S. Application Data

(63) Continuation-in-part of application No. 10/996,100, filed on Nov. 23, 2004.

(51) Int. Cl.
*A61C 5/02* (2006.01)

(52) U.S. Cl. .................................................. 433/102

(58) Field of Classification Search ................ 433/102, 433/141, 143
See application file for complete search history.

(56) References Cited

U.S. PATENT DOCUMENTS

| | | | |
|---|---|---|---|
| 4,155,964 A | | 5/1979 | Aronow |
| 4,202,055 A | * | 5/1980 | Reiner et al. ............ 623/23.57 |
| 4,321,040 A | * | 3/1982 | Miller et al. ................ 433/102 |
| 4,445,810 A | * | 5/1984 | Theilen ...................... 407/118 |
| 4,535,014 A | | 8/1985 | Wright |
| 4,739,536 A | * | 4/1988 | Bandera et al. ................ 16/430 |
| 5,390,572 A | | 2/1995 | Gakhar et al. |
| 5,501,597 A | * | 3/1996 | Wilson ........................ 433/141 |
| 5,516,287 A | | 5/1996 | Zdarsky |
| 5,735,691 A | * | 4/1998 | Fetter ......................... 433/140 |
| 5,775,346 A | * | 7/1998 | Szyszkowski ............... 132/329 |
| 5,775,902 A | * | 7/1998 | Matsutani et al. .......... 433/102 |
| 5,956,799 A | | 9/1999 | Panaccione et al. |
| 6,109,918 A | * | 8/2000 | Hammond et al. ......... 433/141 |
| 6,138,313 A | | 10/2000 | Barton et al. |
| 6,213,771 B1 | | 4/2001 | Fischer |
| 6,257,887 B1 | | 7/2001 | Heckerman et al. |
| 6,276,020 B1 | | 8/2001 | Leversby et al. |
| 6,295,903 B1 | | 10/2001 | Tipper et al. |
| 6,305,937 B1 | | 10/2001 | Williams |
| 6,322,362 B1 | | 11/2001 | Holms |
| 6,322,738 B1 | | 11/2001 | Sicilia et al. |
| 6,353,958 B2 | | 3/2002 | Weihrauch |
| 6,361,317 B1 | * | 3/2002 | Rahman ...................... 433/141 |
| 6,368,536 B1 | * | 4/2002 | Hoepfl et al. ............... 264/250 |
| 6,401,290 B1 | | 6/2002 | Barton et al. |

(Continued)

*Primary Examiner*—Ralph A. Lewis
(74) *Attorney, Agent, or Firm*—Workman Nydegger

(57) ABSTRACT

A dental instrument having a two-shot molded handle and methods for making the same. The dental instrument includes a dental instrument shank of metal with a handle formed near the proximal end of the shank. The handle includes a first polymer formed over a portion of the shank, and a second polymer formed over at least a portion of the first polymer. The first polymer may be rigid so as to more firmly attach to the shank and better resist torsional and/or tensional slippage between the shank and handle during use, while the second polymer may be flexible so as to increase gripability and comfort during manual use of the instrument. The first and second polymers may be of different colors to provide contrast (e.g., to highlight characters formed in the first rigid polymer).

20 Claims, 8 Drawing Sheets

U.S. PATENT DOCUMENTS

| | | |
|---|---|---|
| 6,471,514 B2 * | 10/2002 | Beck et al. .................. 433/141 |
| 6,729,877 B2 * | 5/2004 | Rahman ..................... 433/141 |
| 2003/0203155 A1 | 10/2003 | Kobe et al. |
| 2004/0091714 A1 | 5/2004 | Gunn |
| 2005/0221256 A1 * | 10/2005 | Kangasniemi .............. 433/102 |
| 2006/0063130 A1 * | 3/2006 | Hayman et al. ............ 433/141 |

* cited by examiner

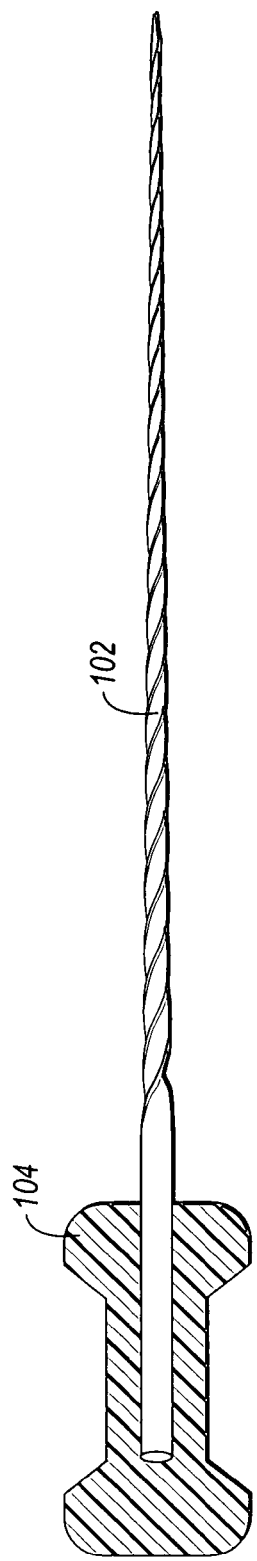
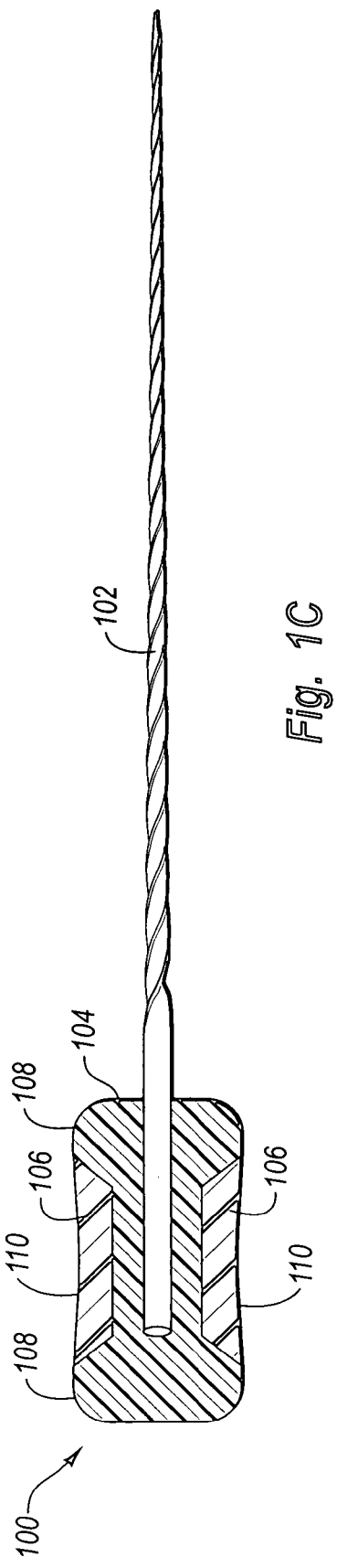
Fig. 1A
Fig. 1B
Fig. 1C

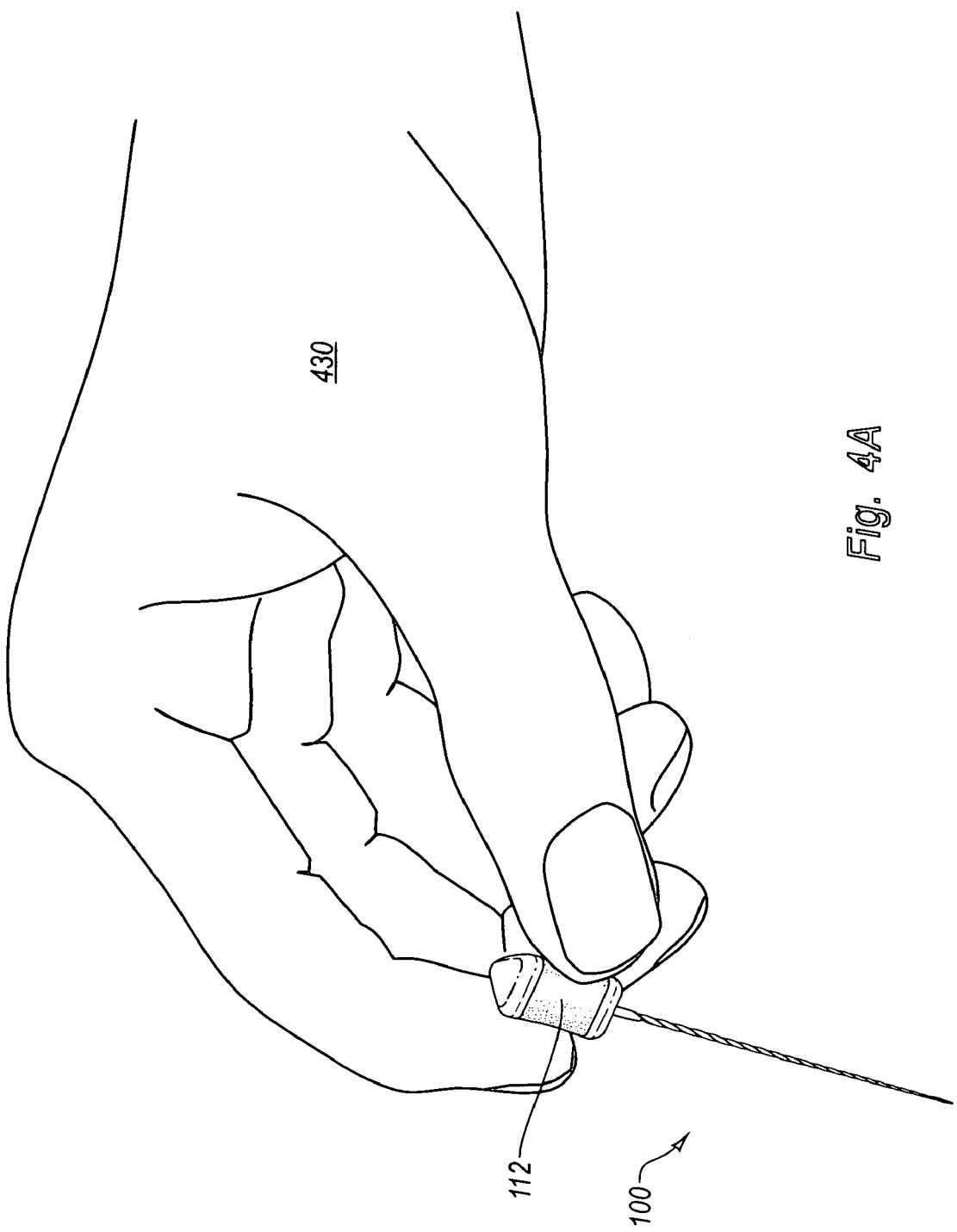

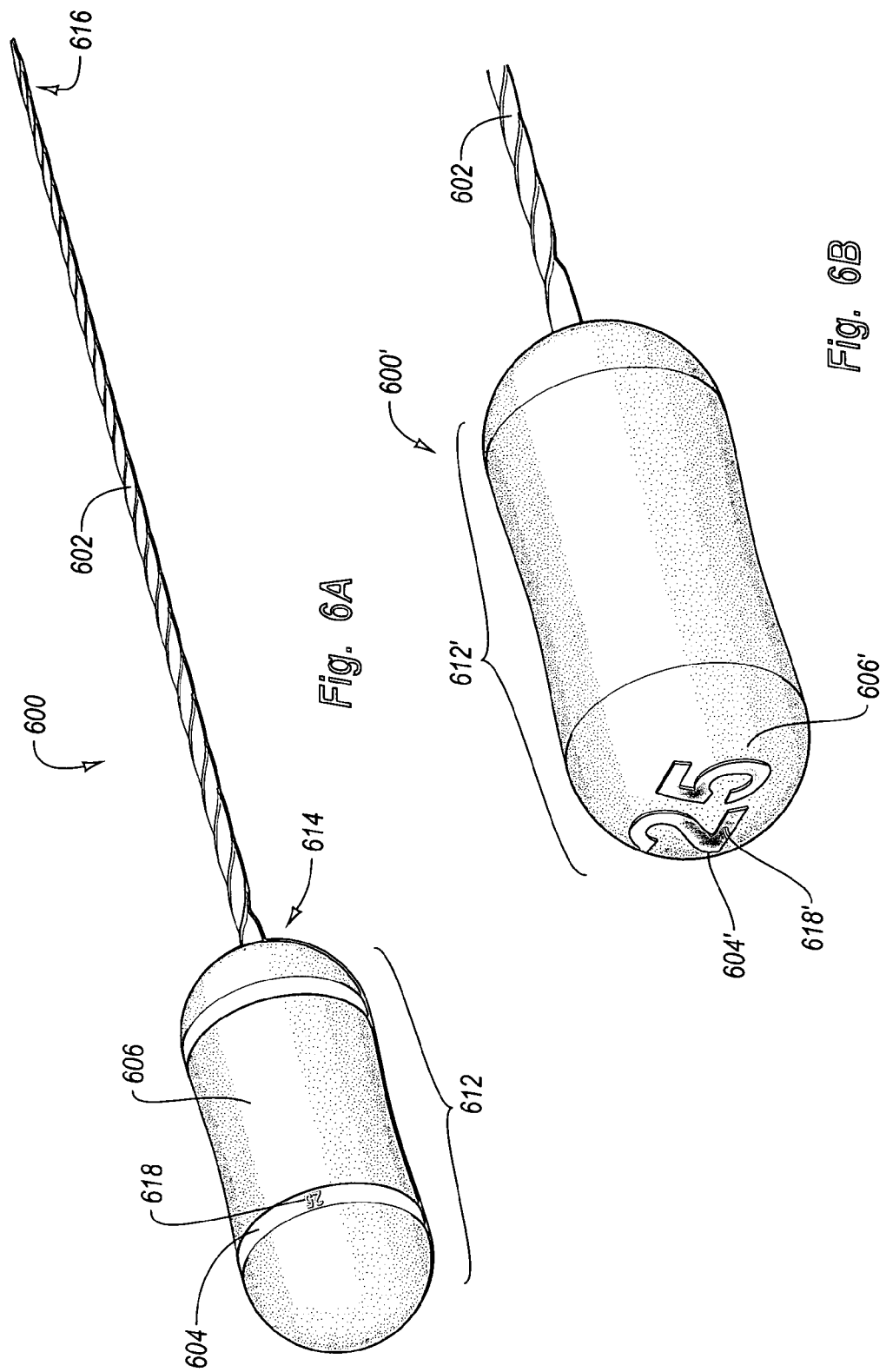

DENTAL INSTRUMENTS HAVING A HANDLE FORMED BY TWO-SHOT MOLDING

RELATED APPLICATIONS

The present application is a continuation-in-part of U.S. patent application Ser. No. 10/996,100, filed Nov. 23, 2004 and entitled "METHOD FOR OVERMOLDING POLYMERS OVER DENTAL TOOLS, the disclosure of which is incorporated by reference in its entirety.

BACKGROUND OF THE INVENTION

1. The Field of the Invention

The invention is in the field of dental instruments and processes for overmolding one or more polymers onto dental instruments (e.g., endodontic files).

2. The Relevant Technology

Dental instruments are often designed to be manually manipulated or to be fitted within a collet of a powered hand piece that provides rotation of an instrument during use. A dental instrument (e.g., an endodontic file) that is intended for hand use is typically provided with an enlarged diameter plastic handle attached to the proximal end of the instrument, configured for manipulation between the thumb and forefinger of the dental practitioner. An instrument intended for use with a powered hand piece has a stem at the instrument proximal end configured to be removably received within a collet of the powered hand piece, by which the instrument may then be rotated as desired by a dental practitioner.

It may be desirable for the enlarged plastic handle of a dental instrument intended for hand use to have a gripable surface. At the same time, dental instruments intended for use with a powered hand piece must include a rigid handle that can be received within a collet.

It would be an improvement in the art to provide dental instruments and methods for manufacturing dental instruments having a two-shot molded handle, at least some of which may include an overmolded handle suitable for manipulation by hand and by a powered hand piece.

BRIEF SUMMARY OF THE PREFERRED EMBODIMENTS

In one aspect, the present invention provides a method for overmolding a plurality of polymers having different properties onto a dental instrument. The method involves providing a dental instrument substrate made of metal, overmolding a first polymer onto a portion of the dental instrument substrate, and then applying a second polymer over a portion of the first polymer. The first polymer is overmolded so that an exposed outer surface of the first polymer corresponds to a portion of the dental instrument to be gripped within a collet of a dental hand piece for powered use. The second polymer is applied so that an exposed outer surface of the second polymer corresponds to a portion of the dental instrument to be gripped by a dental practitioner for manual use.

According to one embodiment, the first polymer may comprise a rigid polymer material. A rigid polymer material provides strength and durability, which is important for portions of the dental instrument that will be subjected to stresses and forces associated with gripping the instrument within the collet of a dental hand piece. Strength and durability will prevent these portions of the dental instrument from cracking or being deformed under stress. According to one embodiment, the rigid polymer material may comprise either a rigid thermoplastic or a rigid chemical cure or thermocure polymer material.

According to one embodiment, the second polymer may comprise an elastomeric material. An elastomeric material provides increased comfort and grippability to portions of the dental instrument that are gripped by a dental practitioner when using the dental instrument manually. According to one embodiment, the elastomeric polymer material may comprise either a thermoplastic elastomer or an elastomeric chemical cure or thermocure polymer material.

The resulting dental instrument includes portions having characteristics of rigidity, strength, and durability, and other portions having characteristics of elasticity, comfort, and grippability. These characteristics allow the dental instrument manufactured according to the inventive method to be used advantageously with a powered hand piece or manually, as desired.

According to one embodiment, the first polymer and second polymer are overmolded and applied respectively so as to form a handle having a trilobular cross sectional configuration. A handle having a trilobular cross sectional configuration is advantageous when manipulating the instrument by hand as it allows the dental practitioner to more easily apply the needed torque. In addition, a trilobular cross sectional configuration also provides improved gripability. A trilobular cross section may also be suitable for use within a powered hand piece.

According to one embodiment, the dental instrument manufactured according to the inventive method may be autoclavable. This may be accomplished according to one embodiment by selecting first and second polymers that are chemically or thermally curable and that have melting and decomposition temperatures that are significantly greater than autoclaving temperatures, which are typically 143° C.

In another aspect, the invention provides a dental instrument having a two-shot molded handle. Such an instrument includes a dental instrument shank formed of metal, and a handle formed near a proximal end of the shank. The handle includes a rigid first polymer formed over a portion of the shank, and a flexible second polymer formed over at least a portion of the first polymer. The rigid first polymer helps attach the handle more firmly to the shank so as to better resist torsional and/or tensional slippage between the shank and the handle during use.

Forming the handle such that it includes a rigid first polymer formed over a portion of the shank provides increased resistance to torsional and/or tensional slippage as compared to a dental instrument including a handle that only includes a flexible polymer formed over the shank. This is because the rigid first polymer has increased strength and durability as compared to flexible polymers. This allows the rigid first polymer to more firmly bond to the shank and to provide better resistance to torsion and/or tension. Resistance to torsion prevents the handle from breaking away and turning independently of the shank during rotation of the instrument, while resistance to tension prevents the handle from pulling off the shank during longitudinal (e.g., vertical) manipulation of the instrument.

Providing the handle with a flexible second polymer formed over at least a portion of the rigid first polymer provides the handle with improved grippability (particularly beneficial for manual use) as compared to a handle that only includes a rigid polymer formed over the shank. Such a dental instrument includes properties of strength and durability (i.e., resistance to torsional and/or tensional slippage) while also being easily grippable and comfortable for manual use.

In one such example of an instrument intended for manual use, the handle may be enlarged so as to facilitate better manual gripping and manual manipulation or instrumentation of the instrument during use. The handle may be enlarged to such a degree so as to not be insertable within a powered handpiece.

In another example (which may or may not include an enlarged handle) the rigid first polymer may be completely encased by the flexible second polymer. Encasing the rigid polymer with a flexible polymer increases the gripping surface area available to the dental practitioner during use.

The dental instruments may include a handle of any desired shape. Exemplary handles may have a substantially triangular cross section (i.e., trilobular), a substantially circular cross section, a substantially square or rectangular cross section, or other cross sectional configuration.

In order to increase and/or provide mechanical interlock between the different portions of the handle, a portion of the proximal end of the dental instrument shank may include a roughened, stamped, or knurled surface so as to form a mechanical interlock between the shank and the rigid first polymer so as to further resist torsional and/or tensional slippage between the shank and the handle during use. In another example, the shank may be bent or twisted (e.g., into a U-, S-, or spiral curve) in order to form such a mechanical interlock between the shank and the rigid first polymer.

In a similar manner, a portion of the rigid first polymer may include a roughened surface so as to form a mechanical interlock between the rigid first polymer and the flexible second polymer so as to increase resistance to torsional and/or tensional slippage between the rigid first polymer portion of the handle and the flexible second polymer portion of the handle.

In one embodiment, a portion of the first polymer may be molded to form an identifying character (e.g., numbers, letters, or other marks identifying the diameter, taper, length, or other characteristics of the instrument) of a first color. The second flexible polymer may be of a second, different color, such that the difference in colors enhances the visual contrast between the identifying character formed of the first polymer and the surrounding or adjacent flexible polymer. The increased visual contrast aids the dental practitioner in identifying the character, particularly when dealing with very small dental instruments (e.g., endodontic files).

These and other benefits, advantages and features of the present invention will become more fully apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings, in which:

FIG. 1A is a perspective view of a dental instrument substrate made of metal;

FIG. 1B is a cross sectional view of the dental instrument substrate of FIG. 1A with a first polymer overmolded onto a portion of the dental instrument substrate;

FIG. 1C is a cross sectional view of the dental instrument substrate of FIG. 1B with a second polymer applied over a portion of the first polymer;

FIG. 4A is a perspective view of the dental instrument of FIG. 2 being held within the hand of a dental practitioner;

FIG. 6A is a perspective view of another dental instrument including a two-shot molded handle;

FIG. 6B is a close-up perspective view of an alternative dental instrument including a two-shot molded handle.

DETAILED DESCRIPTION OF THE PREFERRED EMBODIMENTS

I. Introduction

Figure 2:
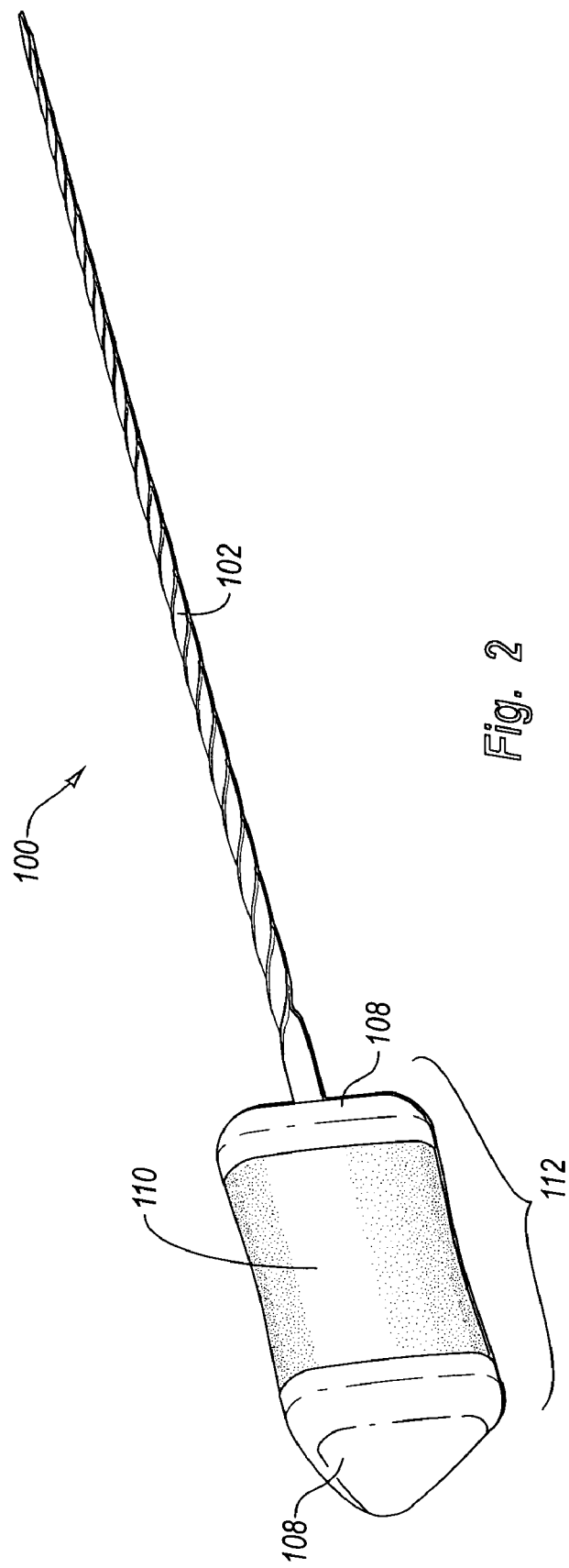
FIG. 2 is a perspective view of an exemplary dental instrument manufactured according to the method of the present invention.

A detailed description of the inventive method and exemplary inventive dental instruments will now be provided, with specific reference to FIGS. 1-7 illustrating preferred embodiments of the invention. It will be appreciated that like structures will be provided with like reference designations.

II. Exemplary Methods of Overmolding Polymers Onto Dental Instruments

FIGS. 1A-1C illustrate an exemplary method of overmolding a plurality of polymers having different properties onto a dental instrument 100. The inventive method involves providing a dental instrument substrate 102 made of metal, as seen in FIG. 1A. A first polymer 104 is overmolded onto a portion of the dental instrument substrate 102, as seen in FIG. 1B. A second polymer 106 is then applied over a portion of the first polymer 104, as seen in FIG. 1C.

The first polymer 104 is overmolded over the dental instrument substrate 102 such that an exposed outer surface 108 of the first polymer 104 corresponds to a portion of the dental instrument 100 to be gripped within a collet of a dental hand piece for powered use. The second polymer 106 is applied over the first polymer 104 such that an exposed outer surface 110 of the second polymer 106 corresponds to a portion of the dental instrument to be gripped by a dental practitioner for manual use. According to one embodiment, the steps of overmolding a first polymer and applying a second polymer may be performed by injection molding, e.g., by a two-color injection molding process.

According to one embodiment, and as illustrated in FIG. 1C, the second polymer 106 may be applied so as to have an exposed outer surface 110 with a concave configuration. The concave configuration may provide increased gripability, while also preventing contact of the surface 110 with the collet of a powered handpiece, which may otherwise rip or tear the exposed outer surface 110.

FIG. 2 illustrates a perspective view of the dental instrument 100 of FIG. 1C. The instrument 100 includes a metallic dental instrument substrate 102. A handle 112 is provided at the proximal end of the metallic dental instrument substrate 102 in order to facilitate manual gripping of the dental instrument 100 by the dental practitioner or mechanical gripping by a dental hand piece (e.g., a reciprocating hand piece).

The handle 112 includes an overmolded first polymer and an applied second polymer. The first polymer includes an exposed outer surface 108 corresponding to a portion of the instrument 100 to be gripped within a collet of a dental hand piece. The second polymer includes an exposed outer surface 110 corresponding to a portion of the instrument 100 to be gripped by a dental practitioner during manual use.

The dental instrument of FIG. 2 includes a handle 112 having a trilobular cross section. A handle 112 having a trilobular cross sectional configuration is advantageous when manipulating the instrument by hand as it allows the dental practitioner to more easily apply the needed torque. In addition, a trilobular configuration provides improved gripability.

Figure 3:
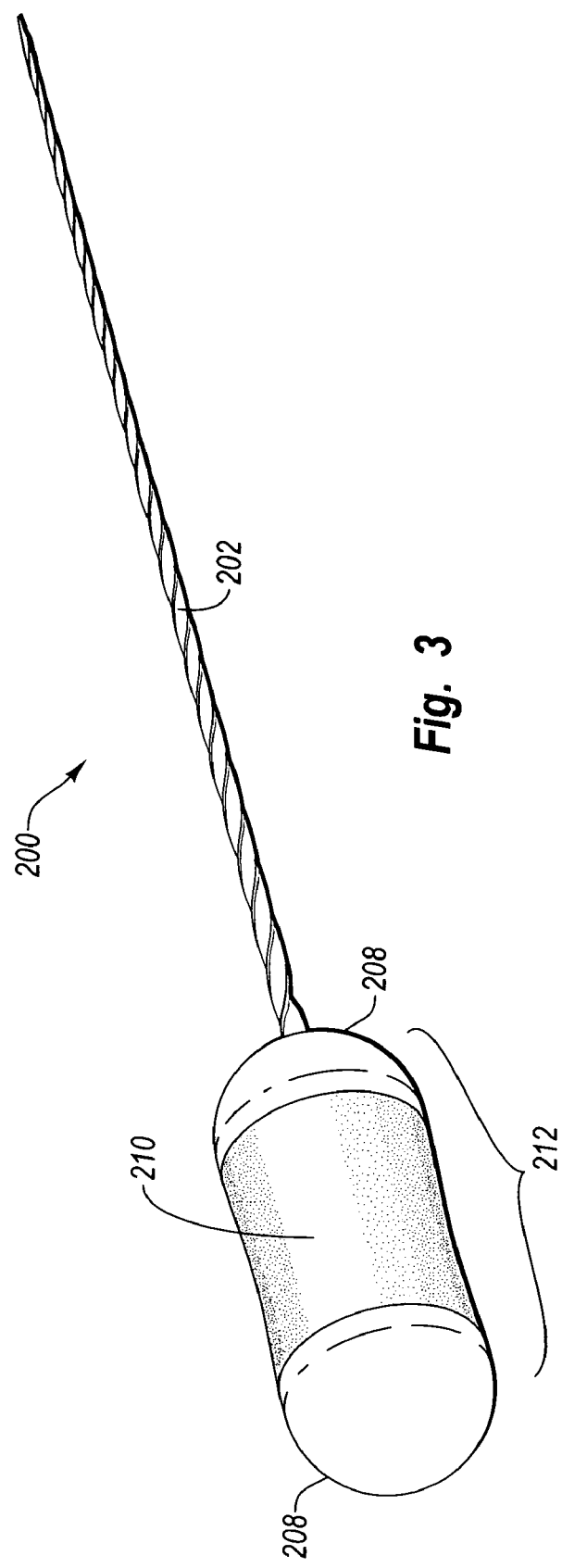
FIG. 3 is a perspective view of an alternative dental instrument manufactured according to the method of the present invention.

FIG. 3 is a perspective view of an alternative embodiment of a dental instrument 200 that includes a dental instrument substrate 202 and a handle 212, which includes an overmolded first polymer and an applied second polymer. The first polymer includes an exposed outer surface 208 corresponding to a portion of the instrument 200 to be gripped within a collet of a dental hand piece. The second polymer includes an exposed outer surface 210 corresponding to a portion of the instrument 200 to be gripped by a dental practitioner during manual use. The handle 212 of dental instrument 200 has a circular cross section. As illustrated, the outer surface 210 may be characterized by a concave curvature.

The outer surfaces 208 and 210 are configured to have specific properties. According to one embodiment, the first polymer comprising outer surface 208 may be a rigid polymer material. A rigid polymer material provides strength and durability, which is important for portions of the dental instrument that will be subjected to stresses and forces associated with gripping the instrument within the collet of a dental hand piece. Strength and durability will prevent these portions of the dental instrument from cracking or being deformed under stress.

According to one embodiment, the rigid polymer material may comprise any rigid thermoplastic material. Suitable rigid thermoplastics include polycarbonates, acrylonitrile butadiene styrene, polyamides, acetals and polysulfones. According to another embodiment, the rigid polymer material may comprise a rigid chemical cure or thermocure polymer material. Besides providing rigidity, strength, and durability, a chemical cure or thermocure polymer material also provides the advantageous characteristic of being autoclavable. Exemplary rigid chemical cure or thermocure polymers include epoxies, phenolics, acrylates, urethanes and polyesters.

According to one embodiment, the second polymer comprising outer surface 210 may be an elastomeric material. An elastomeric material provides increased comfort and gripability to portions of the dental instrument that are gripped by a dental practitioner when using the dental instrument manually. According to one embodiment, the elastomeric polymer material may comprise a thermoplastic elastomer. Alternatively, the elastomeric polymer material may comprise an elastomeric chemical cure or thermocure polymer material for the added advantage of autoclavability.

Examples of suitable thermoplastic elastomers include SARLINK (which comprises EPDM (i.e., ethylene-propylene rubber) particles embedded in a polypropylene matrix), ENGAGE (a polyolefin elastomer), SANTOPRENE (a synthetic rubber), and J-VON (a synthetic rubber). Examples of suitable elastomeric chemical cure or thermocure polymers include silicone rubber, natural rubber, synthetic rubber, and lower durometer urethanes.

The resulting dental instrument includes portions having characteristics of rigidity, strength, and durability, and other portions having characteristics of elasticity, comfort, and grippability. These characteristics allow the dental instrument manufactured according to the inventive method to be used advantageously with a powered hand piece or manually, as desired.

FIG. 4A illustrates dental instrument 100 being gripped manually by a dental practitioner's hand 430. The trilobular configuration of handle 112 allows the dental practitioner to more easily apply the needed torque during use.

Figure 4C:
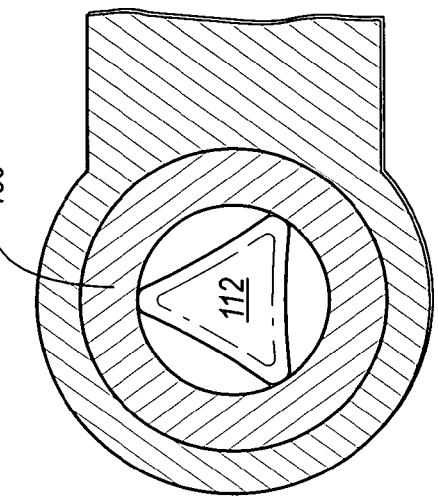
FIG. 4C is a cross sectional view of the dental instrument and powered hand piece of FIG. 4B taken along cutting line 4C-4C.
Figure 4B:
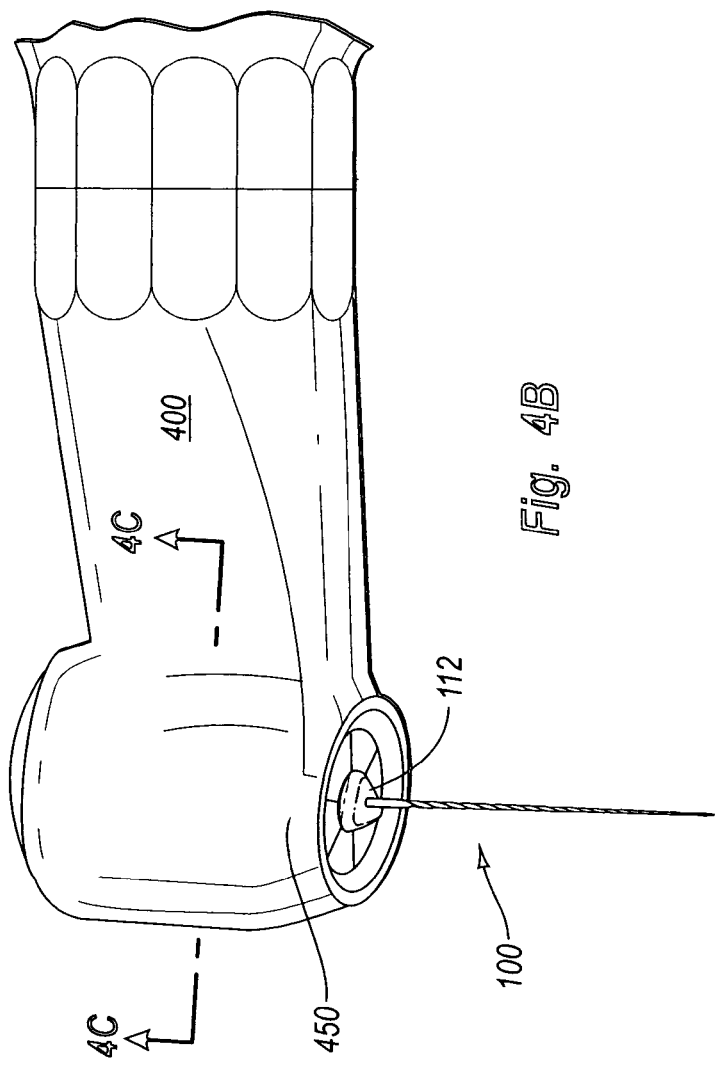
FIG. 4B is a perspective view of the dental instrument of FIG. 2 being held within a collet of a powered hand piece.

Referring to FIGS. 4B and 4C, a trilobular handle configuration is also suitable for use within a powered hand piece. FIG. 4B illustrates dental instrument 100 having a trilobular handle 112 received within a collet 450 of a powered hand piece 400. As best seen in FIG. 4C, the lobes of the handle 112 are received within and securely held by the (e.g., round) collet 450 of the hand piece 400. The exposed outer surface 110 of the relatively soft second polymer is not in gripping contact with the collet 450 of the handpiece 400, which might otherwise tear, rip, or deform the relatively soft second polymer.

According to one embodiment, the dental instruments manufactured according to the inventive method may be autoclavable. This may be accomplished according to one embodiment by selecting first and second polymers that are chemically or thermally curable and that have melting and decomposition temperatures that are significantly greater than autoclaving temperatures (e.g., typically about 143° C.).

III. Additional Exemplary Dental Instruments

Figure 5A:
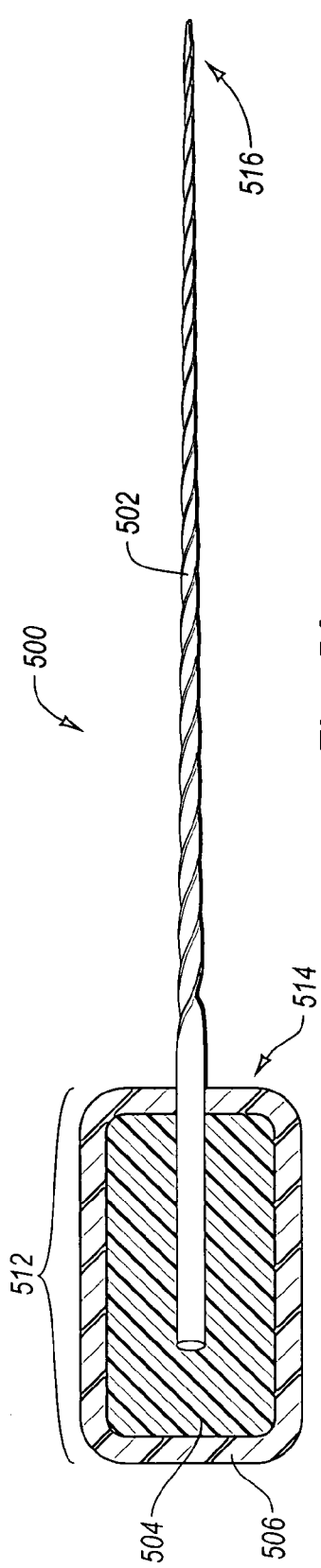
FIG. 5A is a cross sectional view of another alternative dental instrument including a two-shot molded handle.
Figure 5B:
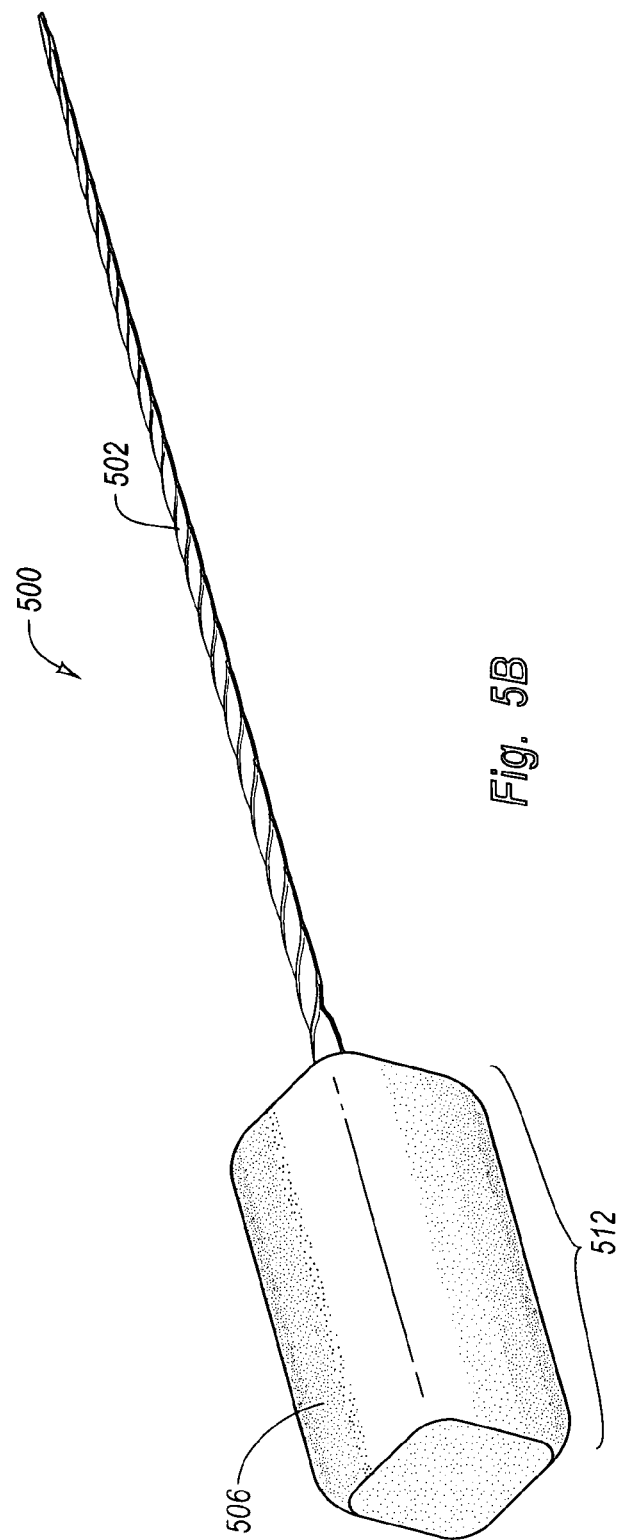
FIG. 5B is a perspective view of the dental instrument of FIG. 5A including a handle having a rectangular cross section.

FIGS. 5A and 5B illustrate an alternative dental instrument 500 having a two-shot molded handle 512 and a metallic dental instrument shank 502 including a proximal end 514 and a distal end 516. Handle 512 is formed near proximal end 514 of shank 502. Handle 512 includes a rigid first polymer 504 formed over a portion of shank 502, and a flexible second polymer 506 formed over at least a portion of first polymer 504. As described above, rigid first polymer 504 has good strength and durability (particularly as compared to flexible polymers). This allows the rigid first polymer to more firmly attach to shank 502 so as to better resist torsional and/or tensional slippage between shank 502 and handle 512, particularly as compared to a handle that only includes a grip enhancing flexible polymer formed over shank 502.

Dental instrument 500 is illustrated as including an enlarged handle 512, which facilitates better manual gripping and manipulation of the instrument during use. In some embodiments, the handle may be so large as to not be insertable within a collet of a powered handpiece.

As illustrated in FIGS. 5A and 5B, handle 512 of dental instrument 500 may be formed such that second polymer 506 completely encases rigid first polymer 504. Such an embodiment may be particularly suited for manual use, having an increased surface area covered by flexible second polymer 506, while also having increased resistance to torsional and/or tensional slippage between shank 502 and handle 512.

Although illustrated as having a substantially square cross section, it is to be understood that handle 512 (as well as any of the handles disclosed) may be of any desired shape. Alternative handles may be have a substantially triangular cross section (i.e., trilobular), a substantially circular cross section, a substantially rectangular cross section, or other cross sectional configuration.

FIG. 6A illustrates another dental instrument 600 having a two-shot molded handle 612 and a metallic dental instrument shank 602 including a proximal end 614 and a distal end 616. Handle 612 includes a rigid first polymer 604 formed over proximal end 614 of shank 602, and a flexible second polymer 606 formed over a portion of rigid first polymer 604. A portion of rigid first polymer 604 is molded so as to form an identifying character 618 (e.g., numbers, letters, or other marks). The identifying character 618 may identify the diameter, taper, length, or any other desired characteristics of instrument 600. Flexible second polymer 606 is formed over much of first polymer 604. Rigid first polymer 604 may be of a first color, while flexible second polymer 606 is of a different, second color. In such an embodiment, the difference in color between rigid first polymer 604 and flexible second polymer 606 increases or enhances the visual contrast between identifying character 618 and the surrounding or adjacent second color of second polymer 606. This increased visual contrast (as compared to if the identifying character and surrounding/adjacent areas were all of the same color) aids the dental practitioner in identifying the character 618, particularly if dental instrument 600 is very small.

In addition, the ability to form an identifying character 618 having enhanced contrast during the molding of handle 612 reduces the cost and steps required as compared to a process in which an identifying character of a different color is added (e.g., by ink) after the handle has been formed.

FIG. 6B illustrates another dental instrument 600' having a two-shot molded handle 612' and a metallic dental instrument shank 602'. Handle 612' includes a rigid first polymer 604' formed over a portion of shank 602', and a flexible second polymer 606' formed over a portion of rigid first polymer 604'. A portion of rigid first polymer 604' is molded so as to form an identifying character 618'. Character 618' is located on the proximal end of handle 612', and is quite large (relative to the character 618 of FIG. 6A). Such placement and sizing may be particularly advantageous when a plurality of differently sized instruments are arranged together in a vertical orientation, allowing the dental practitioner to easily identify the character at the proximal end of each handle.

In the illustrated embodiment, flexible second polymer 606' is formed over all of first polymer 604' except that portion forming character 618'. Rigid first polymer 604' may be of a first color (e.g., a dark color), while flexible second polymer 606' is of a different, second color (e.g., a light color). In such an embodiment, the difference in color between rigid first polymer 604' and flexible second polymer 606' increases or enhances the visual contrast between identifying character 618' and the surrounding or adjacent second color of second polymer 606', particularly because the second color surrounds the first color of the identifying character 618'.

Figure 7:
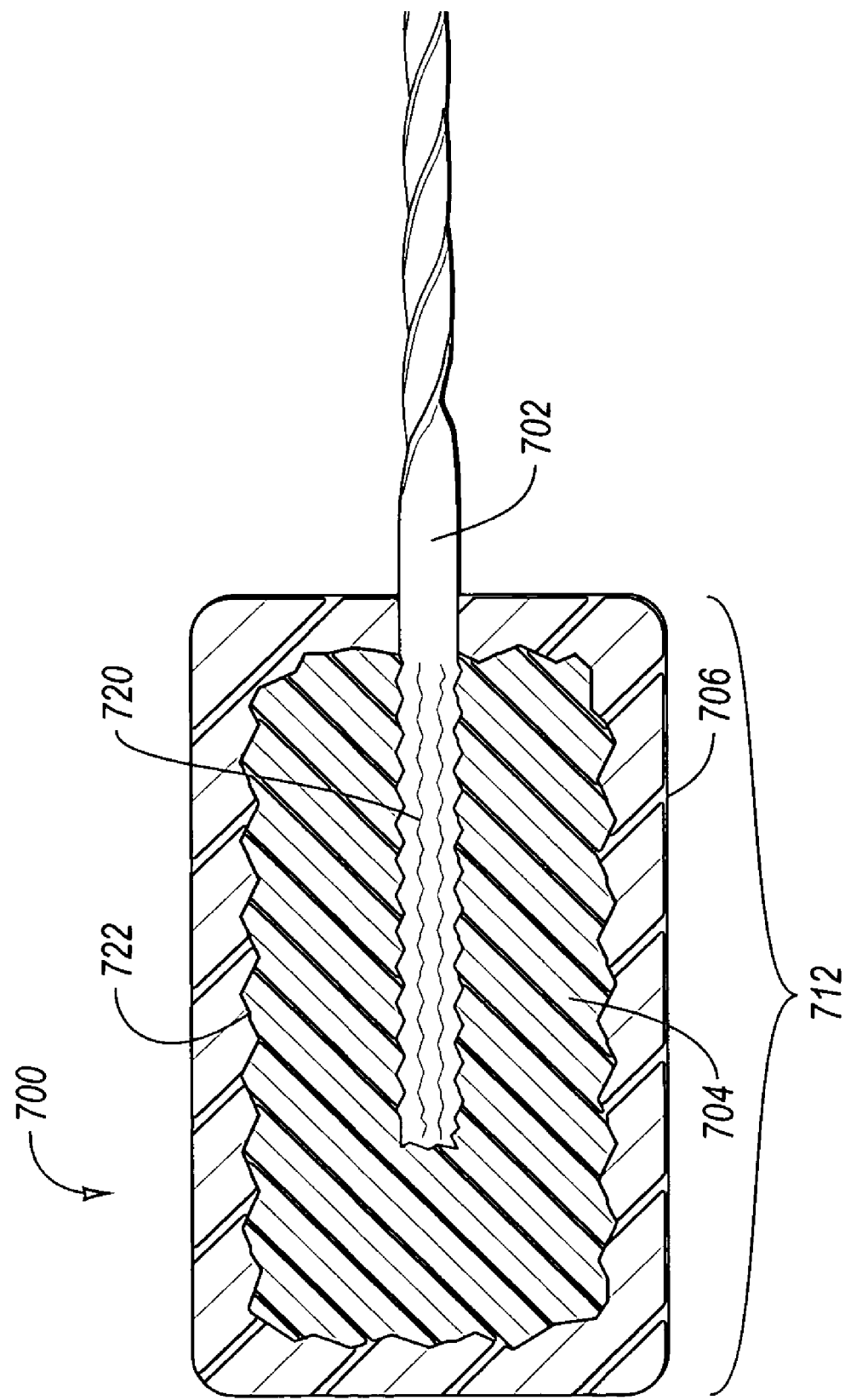
FIG. 7 is a close up cross-sectional view of a proximal end of another dental instrument.

FIG. 7 illustrates a cross sectional view of the proximal portion of a dental instrument 700 including a metallic shank 702 and a handle 712. The shank 702 is illustrated as including a roughened surface 720 so as to form a mechanical interlock between shank 702 and rigid first polymer 704. Roughened surface 720 provides increased mechanical bonding between shank 702 and rigid first polymer 704 in addition to any chemical bonding present. Although illustrated as having a roughened surface, it is to be understood that proximal end 714 of shank 702 may be roughened, stamped, knurled, or even bent or twisted (e.g., into a U or S-curve) in order to provide increased mechanical interlock between shank 702 and rigid first polymer 704. Roughening, stamping, knurling, bending or twisting shank 702 are all examples of means for increasing mechanical interlock between the shank and the rigid first polymer.

Rigid first polymer 704 of handle 712 is illustrated as also including a roughened surface 722 at the interface between rigid first polymer 704 and flexible second polymer 706. Such a roughened surface provides increased mechanical interlock between rigid first polymer 704 and flexible second polymer 706 so as to further increase the ability of dental instrument 700 to resist torsional and/or tensional slippage that might otherwise occur.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A dental instrument having a two-shot molded handle, comprising:
    a dental instrument shank made of metal having a proximal end and a distal end, the shank having a diameter so as to be at least partially insertable into a root canal of a tooth;
    a handle formed at or near the proximal end of the dental instrument shank by a two-shot molding process, the handle comprising:
        a rigid first polymer formed by molding over a portion of the shank at or near the proximal end of the shank; and
        a flexible second polymer formed by molding over at least a portion of the rigid first polymer in order to form a spaceless interface between the rigid first polymer and the flexible second polymer; and
    means, disposed on a surface of the dental instrument shank at or near the proximal end, for increasing mechanical interlock between the shank and the rigid first polymer so as to better resist torsional and/or tensional slippage between the shank and the handle during use compared to a dental instrument lacking the means for increasing mechanical interlock,
    wherein the rigid first polymer helps attach the handle more firmly to the shank compared to the flexible second polymer so as to better resist torsional and/or tensional slippage between the shank and the handle during use compared to a dental instrument in which only the second polymer is formed over the shank.

2. A dental instrument as recited in claim 1, wherein the rigid first polymer is completely encased by the flexible second polymer.

3. A dental instrument as recited in claim 1, wherein the first and second polymers form an enlarged handle that facilitates manual instrumentation.

4. A dental instrument as recited in claim 1, wherein the first and second polymers form a handle having a substantially triangular cross section.

5. A dental instrument as recited in claim 1, wherein the first and second polymers form a handle having a substantially circular cross section.

6. A dental instrument as recited in claim 1, wherein the first and second polymers form a handle having a substantially rectangular cross section.

7. A dental instrument as recited in claim 1, wherein the means for increasing mechanical interlock comprises a roughened, stamped, knurled, bent or twisted portion of the shank over which the rigid first polymer is formed.

8. A dental instrument as recited in claim 1, wherein a portion of the rigid first polymer includes a roughened surface so as to form a mechanical interlock between the rigid first polymer and the flexible second polymer so as to better resist torsional and/or tensional slippage between the flexible second polymer and the rigid first polymer during use.

9. A dental instrument as recited in claim 1, wherein a portion of the first polymer forms an identifying character of a first color, wherein a portion of the second polymer is immediately adjacent to the identifying character so as to fill in any spaces around and/or within the identifying character, and wherein the second polymer is of a second color so as to provide contrast between the identifying character and the second polymer so as to facilitate identification of the identifying character.

10. A dental instrument as recited in claim 1, wherein the rigid first polymer comprises a rigid thermoplastic polymer.

11. A dental instrument as recited in claim 10, wherein the rigid thermoplastic polymer comprises at least one member selected from the group consisting of polycarbonates, acrylonitrile butadiene styrene, polyamides, acetals and polysulfones.

12. A dental instrument as recited in claim 1, wherein the rigid first polymer comprises a rigid chemical cure or thermocure polymer.

13. A dental instrument as recited in claim 12, wherein the rigid chemical cure or thermocure polymer comprises at least one member selected from the group consisting of epoxies, phenolics, acrylates, urethanes, and polyesters.

14. A dental instrument as recited in claim 1, wherein the flexible second polymer includes an exposed outer surface that enhances grip by a dental practitioner.

15. A dental instrument as recited in claim 1, wherein the flexible second polymer comprises a thermoplastic elastomer.

16. A dental instrument as recited in claim 15, wherein the thermoplastic elastomer comprises at least one member selected from the group consisting of polyolefin-based elastomers and synthetic rubbers.

17. A dental instrument as recited in claim 1, wherein the flexible second polymer comprises an elastomeric chemical cure or thermocure elastomer.

18. A dental instrument as recited in claim 17, wherein the elastomeric chemical cure or thermocure elastomer comprises at least one member selected from the group consisting of silicone rubbers, natural rubbers, synthetic rubbers, and lower durometer polyurethanes.

19. A dental instrument having a two-shot molded handle, comprising:
a dental instrument shank made of metal having a proximal end and a distal end, the shank having a diameter so as to be at least partially insertable into a root canal of a tooth; and
a handle formed near the proximal end of the dental instrument shank by a two-shot molding process, the handle comprising:
a rigid first polymer of a first color formed by molding over a portion of the shank; and
a flexible second polymer of a second color formed by molding over at least a portion of the first polymer in order to form a spaceless interface between the rigid first polymer and the flexible second polymer;
wherein a portion of the rigid first polymer at an end face of the handle opposite the shank forms an identifying character which is visibile to an observer during use of the dental instrument while placed within a root canal and held between a person's fingers,
wherein a portion of the flexible second polymer at the end face of the handle is immediately adjacent to the identifying character so as to fill in any spaces around and/or within the identifying character in order for the second color of the second polymer to provide contrast between the identifying character and the second polymer so as to facilitate visual identification of the identifying character.

20. A dental instrument having a two-shot molded handle, comprising:
a dental instrument shank made of metal having a proximal end and a distal end; and
an enlarged handle formed by a two-shot molding process near the proximal end of the dental instrument shank and configured solely for manual instrumentation and not for insertion into a collet of a powered dental handpiece, the enlarged handle comprising:
a rigid first polymer formed by molding over a portion of the shank; and
a flexible second polymer formed by molding over the first polymer so as to completely encase the rigid first polymer in order to form a spaceless interface between the rigid first polymer and the flexible second polymer;
wherein the rigid first polymer helps attach the handle more firmly to the shank compared to the flexible second polymer so as to better resist torsional and/or tensional slippage between the shank and the handle during use,
wherein a portion of the rigid first polymer includes a roughened surface so as to form a mechanical interlock between the rigid first polymer and the flexible second polymer so as to better resist torsional and/or tensional slippage between the flexible second polymer and the rigid first polymer during use.

* * * * *

UNITED STATES PATENT AND TRADEMARK OFFICE
CERTIFICATE OF CORRECTION

PATENT NO.        : 7,234,939 B2                              Page 1 of 2
APPLICATION NO. : 11/205593
DATED             : June 26, 2007
INVENTOR(S)       : Dan J. Bills It is certified that error appears in the above-identified patent and that said Letters Patent is hereby corrected as shown below:

Title Page
Abstract, Line 11, change "gripability" to --grippability--

In the Drawings:
Figures
Sheet 7, replace FIG. 6B with the figure depicted herein below, wherein "602" has been changed to --602'--

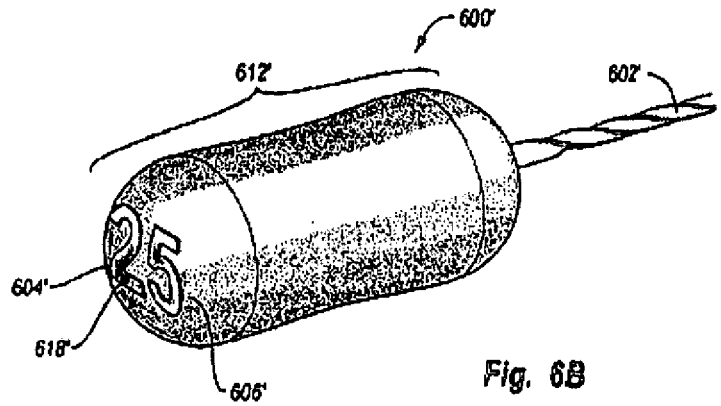

Sheet 8, replace FIG. 7 with the figure depicted herein below, wherein --714-- has been added to show the "proximal end"

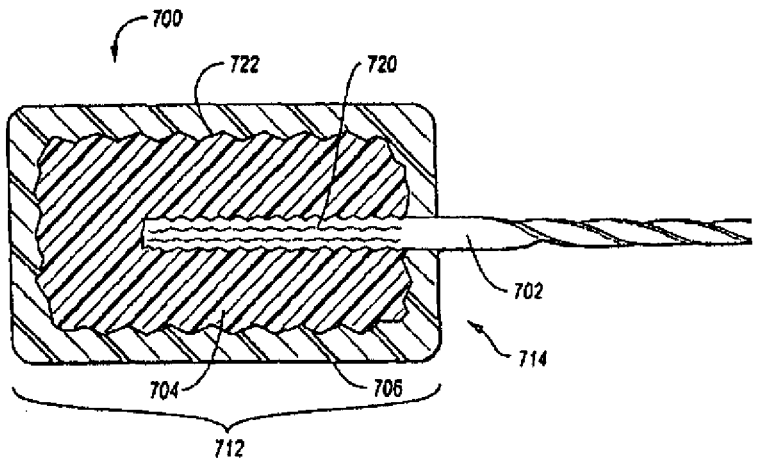

UNITED STATES PATENT AND TRADEMARK OFFICE
CERTIFICATE OF CORRECTION

PATENT NO. : 7,234,939 B2
APPLICATION NO. : 11/205593
DATED : June 26, 2007
INVENTOR(S) : Dan J. Bills It is certified that error appears in the above-identified patent and that said Letters Patent is hereby corrected as shown below:

Column 1
Line 34, change "gripable" to --grippable--

Column 2
Line 27, change "gripability" to --grippability--

Column 5
Line 2, change "gripability" to --grippability--
Line 26, change "gripability" to --grippability--

Column 7
Line 10, remove [be]

Signed and Sealed this

Twenty-fourth Day of November, 2009

David J. Kappos
*Director of the United States Patent and Trademark Office*